United States Patent
Hahn et al.

(10) Patent No.: US 10,548,847 B2
(45) Date of Patent: Feb. 4, 2020

(54) COMPOSITION FOR MANUFACTURING ORALLY DISINTEGRATING DOSAGE FORM TO PROTECT COATING LAYER OF ACTIVE SUBSTANCE

(71) Applicant: CHOONGWAE PHARMA CORPORATION, Seoul (KR)

(72) Inventors: Mikyoung Hahn, Seoul (KR); Jin-Woo Choi, Seoul (KR); Dae-Hyeon Kim, Seoul (KR)

(73) Assignee: CHOONGWAE PHARMA CORPORATION, Seoul (KR)

( * ) Notice: Subject to any disclaimer, the term of this patent is extended or adjusted under 35 U.S.C. 154(b) by 1019 days.

(21) Appl. No.: 14/803,546

(22) Filed: Jul. 20, 2015

(65) Prior Publication Data

US 2016/0030357 A1    Feb. 4, 2016

Related U.S. Application Data

(62) Division of application No. 12/671,981, filed as application No. PCT/KR2008/001405 on Mar. 12, 2008, now abandoned.

(30) Foreign Application Priority Data

Aug. 3, 2007    (KR) .................. 10-2007-0078175
Feb. 22, 2008    (KR) .................. 10-2008-0016315

(51) Int. Cl.
| | | |
|---|---|---|
| *A61K 9/20* | (2006.01) | |
| *A61K 9/00* | (2006.01) | |
| *A61K 9/50* | (2006.01) | |
| *A61K 31/166* | (2006.01) | |
| *A61K 31/192* | (2006.01) | |
| *A61K 31/4184* | (2006.01) | |
| *A61K 31/454* | (2006.01) | |
| *A61K 31/519* | (2006.01) | |
| *A61K 31/5375* | (2006.01) | |
| *A61K 47/26* | (2006.01) | |
| *A61J 3/00* | (2006.01) | |
| *A61J 3/10* | (2006.01) | |

(52) U.S. Cl.
CPC .............. *A61K 9/2095* (2013.01); *A61J 3/10* (2013.01); *A61K 9/0053* (2013.01); *A61K 9/0056* (2013.01); *A61K 9/2081* (2013.01); *A61K 9/5026* (2013.01); *A61K 9/5047* (2013.01); *A61K 9/5078* (2013.01); *A61K 31/166* (2013.01); *A61K 31/192* (2013.01); *A61K 31/4184* (2013.01); *A61K 31/454* (2013.01); *A61K 31/519* (2013.01); *A61K 31/5375* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 5,651,984 | A | 7/1997 | Powell |
| 5,780,055 | A | 7/1998 | Habib et al. |
| 6,020,002 | A | 2/2000 | Myers et al. |
| 6,270,790 | B1 | 8/2001 | Robinson et al. |
| 6,858,725 | B1 | 2/2005 | Vladyka et al. |
| 6,923,984 | B1 | 8/2005 | Remon |
| 2002/0071865 | A1 | 6/2002 | Kajiyama et al. |
| 2005/0232988 | A1 | 10/2005 | Venkatesh et al. |
| 2007/0092564 | A1 | 4/2007 | Li et al. |

FOREIGN PATENT DOCUMENTS

| | | |
|---|---|---|
| EP | 1 300 420 A1 | 4/2003 |
| JP | 8-333242 A | 12/1996 |
| KR | 1998-085592 A | 12/1998 |
| KR | 2000-0016654 A | 3/2000 |
| KR | 2002-0069377 A | 9/2002 |
| KR | 10-2004-0011087 A | 2/2004 |
| KR | 10-2004-0073288 | 8/2004 |
| KR | 10-2005-0096941 A | 10/2005 |
| KR | 20050118775 A | 12/2005 |
| WO | WO 9725029 A1 | 7/1997 |
| WO | WO 2005105047 A1 | 11/2005 |

OTHER PUBLICATIONS

Tunon, Comprehensive Summaries of Uppsala Dissertations from the Faculty of Pharmacy, 288, pp. 1-65 (2003).*
A. Debunne et al., "Development and in Vitro Evaluation of an Enteric-Coated Multiparticulate Drug Delivery System for the Administration of Piroxicam to Dogs," European Journal of Pharmaceutics, vol. 54, pp. 343-348, 2002.
R. Bodmeier, "Tableting of Coated Pellets," European Journal of Pharmaceutics and Biopharmaceutics, vol. 43, pp. 1-8, 1997.
T. E. Beckert et al., "Compression of Enteric-Coated Pellets to Disintegrating Tablets," International Journal of Pharmaceuitics, vol. 143, pp. 13-23, 1996.
Lundqvist et al., European Journal of Pharmaceutics and Biopharmaceutics, 46: 369-379 (1998).
Gupta et al., JK Science, 6 : 106-108 (2004).
Indian Office Action dated Sep. 4, 2015 for corresponding Indian Application No. 768/KOLNP/2010.

* cited by examiner

*Primary Examiner* — Bethany P Barham
*Assistant Examiner* — Barbara S Frazier
(74) *Attorney, Agent, or Firm* — Blank Rome LLP

(57) ABSTRACT

The present invention relates to a method of manufacturing an orally disintegrating dosage form which masks a bitter or unpleasant taste. A composition including a ratio of excipients and a coated active substance prevents a coating layer on the active substance from being destroyed during manufacture.

18 Claims, No Drawings

US 10,548,847 B2

COMPOSITION FOR MANUFACTURING ORALLY DISINTEGRATING DOSAGE FORM TO PROTECT COATING LAYER OF ACTIVE SUBSTANCE

This application is a divisional of U.S. patent application Ser. No. 12/671,981, filed Feb. 3, 2010, and which is incorporated by reference in its entirety. This application is based on and claims priority from Korean patent application numbers 10-2007-0078175, filed Aug. 3, 2007 and 10-2008-0016315, filed Feb. 22, 2008, through U.S. patent application Ser. No. 12/671,981 and PCT/KR2008/001405, filed Mar. 12, 2008, the disclosures of which are hereby incorporated by reference herein in their entireties.

TECHNICAL FIELD

The present invention relates to a composition of an orally disintegrating dosage form that is used to protect a coating layer of an active substance from being destroyed during a tableting process.

BACKGROUND ART

As a method for preventing a bitter taste or an unpleasant taste, addition of a flavored sweetener, manufacturing of a solid dispersion by using a spray dryer, shielding by using an ion exchange resin, melt extrusion, coating by fluidized bed water, and so forth have been known. In addition to that, various types of technologies, in which an active substance is coated with a polymer that is not dissolved in the oral cavity to prevent a patient from feeling a bitter taste in the oral cavity or the gullet when administered, have been known.

Korean Patent Application Publication No. 10-2004-0011087 a process for preparing roxithromycin granules having masked taste and smell" relates to a method of manufacturing a roxithromycin granule, which comprises granulating an active substance, roxithromycin, and then fine-coating the granulated roxithromycin, which in turn serves as a seed in coating with an agent and a plasticizer at low temperatures. The patent discloses that an unpleasant taste and flavor are masked and an active substance is released only in the stomach. Korean Patent Application Publication No. 2002-0069377 that has the invention title of "a process for preparing release-controlled granules of quinolone-based drugs having masked taste and smell" discloses a process in which an active substance is granulated and the taste and flavor are masked by using a fluidized bed water.

In accordance with the demand for novel medicinal products that can be easily taken and have improved convenience, various types of methods for manufacturing an orally disintegrating dosage form have been developed in many countries. Korean Patent Application Publication No. 2000-0016654 that has the invention title of "intraorally rapidly disintegrable tablet" discloses a method for manufacturing a tablet that contains sugar alcohol or sugars having an average particle diameter of 30 μm or less, an active substance, and a disintegrating agent. Korean Patent Application Publication No. 10-2004-0073288 that has the invention title of "solid orally-dispersible pharmaceutical formulation" discloses a method for manufacturing a solid orally dispersible pharmaceutical formulation comprising granules of co-dried lactose and starch and an active substance. In addition, Korean Patent Application Publication No. 10-2005-0096941 that has the invention title of "tablet quickly melting in the oral cavity" discloses a method of providing a tablet that has the hardness, which is considered to be desirable in practice, and rapidly integrates in the oral cavity. The above-mentioned prior arts disclose the methods for manufacturing the orally disintegrating dosage form, but they do not disclose how to mask a taste and a flavor of an active substance. When an orally disintegrating dosage form is manufactured according to the above-mentioned methods after an active substance having bitter or unpleasant taste is covered with the coating layer, the coating layer of the active substance is destroyed by pressure, thus a patient may feel the taste of the active substance. Thus, there is a disadvantage in that dosage and convenience performances may not be improved.

With respect to a method for protecting contents during tableting, U.S. Pat. No. 6,923,984 B1 that has the invention title of "Cushioning wax beads for making solid shaped articles" discloses a method for protecting wax beads containing an active substance by controlling the ratio of similar-sized cushioning wax beads. However, there are disadvantages in that it requires high shear mixing with temperature-control and that $CO_2$ pellet needs to be supplied for temperature control.

DISCLOSURE OF INVENTION

Technical Problem

A coating layer of an active substance, e.g. for preventing a bitter or an unpleasant taste and so forth, may easily be destroyed by pressure applied during a tableting process. It is an object of the present invention to provide a composition of an orally disintegrating dosage form that is used to protect a coating layer on an active substance from being destroyed during a tableting process.

Technical Solution

The present invention relates to a composition of an orally disintegrating dosage form that is used to protect a coating layer of an active substance from being destroyed during a tableting process.

The pharmaceutical composition comprises:
a coated active substance;
a buffer having a hardness that is lower than the coated active substance; and
a shield having a hardness that is higher than the coated active substance and a particle size that is larger than the coated active substance. It is preferable that the dosage form be a tablet.

According to an embodiment, the hardness of the buffer is 0.1 times or more and less than 1 time as high as the hardness of the particle of the coated active substance, and preferably 0.1 to 0.7 times as high as the hardness of the particle of the coated active substance. The hardness of the shield is more than 1 time and 20 times or less as high as the hardness of the particle of the coated active substance, and preferably 4 to 15 times as high as the hardness of the particle of the coated active substance.

According to another embodiment, the coated active substance has the particle diameter in the range of 0.1 to 1000 μm, and preferably in the range of 150 to 425 μm. The buffer has the particle diameter which is 0.1 to 10 times as large as the particle diameter of the coated active substance, and preferably 1 to 3 times as large as the particle diameter of the coated active substance. The shield has the particle diameter which is more than 1 time and 10 times or less as large as the particle diameter of the coated active substance, and preferably more than 1 time and 4 times or less as large as the particle diameter of the coated active substance.

According to another embodiment, the weight ratio of the buffer with respect to the coated relive substance is 5 or less, and the weight ratio of the shield with respect to the coated active substance is 3 or less. It is preferable that the weight of the above coated active substance be in the range of 1 to 1000 mg, the weight ratio of the buffer be in the range of 0.1 to 3 with respect to the above coated active substance, and the weight ratio of the shield be in the range of 0.1 to 2. More preferably, the weight ratio of the buffer with respect to the shield is 1 or more.

Examples of the shape of the buffer or the shield may include: powder; fine crystals; granules that are formed by using dry, wet, or high temperature granulation; or particles that are formed by using mounting on a neutral support body or extrusion, but the shape is not limited thereto.

The buffer and the shield each independently are manufactured by granulating a material selected from isomalt, mannitol, dried mannitol, crystalline mannitol, maltitol, lactose, glucose, lactitol, trehalose, dextrate, white sugar, white sugar for direct tableting, sorbitol, xylitol, mannitol granules, aspartame, acesulfame, acesulfame potassium, saccharin sodium, a cellulose polymer, and a mixture thereof, but the material is not limited thereto.

The coating layer of the coated active substance may be manufactured by: a coating method using a fluidized bed water; a coating method using a spray drier; coagulation coating; microencapsulation; micro-granulation; ionic resin absorption process; or coating by a polymer after an active substance is applied on a seed, but the manufacturing of the coating layer is not limited thereto.

Preferably, the orally disintegrating dosage form disintegrates in the oral cavity within 60 seconds. More preferably, the orally disintegrating dosage form disintegrates into particles having a diameter of 2 mm or less within 60 seconds.

Preferably, the hardness of the orally disintegrating dosage form is 30 N or more.

In addition, the present invention provides a method for manufacturing an orally disintegrating dosage form by using the pharmaceutical composition. Specifically, the orally disintegrating dosage form is manufactured by a tableting process, and pressure is applied to the pharmaceutical composition during the tableting process so that the buffer is destroyed but the coated active substance and the shield is not destroyed.

Advantageous Effects

In an orally disintegrating dosage form that is manufactured by using a composition of the present invention, a coating layer of an active substance is protected against pressure during a tableting process. Thus, a patient can take the orally disintegrating dosage form having undamaged coating layer.

BEST MODE FOR CARRYING OUT THE INVENTION

As means for protecting a coating layer from being destroyed, the composition of the present invention comprises, at a predetermined mixing ratio, (a) a "buffer" having a hardness that is lower than that of a coated active substance and (b) a "shield" having a higher hardness and larger particle diameter than the coated active substance. The buffer is an excipient that performs buffer action by being destroyed before the coating layer is destroyed in order to prevent the coated active substance from being destroyed by pressure that is applied during the tableting process. The buffer is 0.1 to 10 times larger in diameter than the coated active substance and it has the hardness that is less than 1 time as high as that of the coated active substance, and is used at a weight ratio of 5 or less with respect to the weight of the coated active substance. The shields, which have the higher hardness and larger particle diameter than the coated active substance, preclude pressure from being applied to the active substances while the buffers, which are destroyed by the pressure, are disposed in spaces formed during the tableting process. The shield has the particle size that is 1 to 10 times larger in diameter that the coated ac rive substance and the hardness that is 1 to 20 times higher than the coated active substance, and it is used at a weight ratio of 3 or less with respect to the weight of the coated arrive substance. Thereby, the present invention provides a method for manufacturing an orally disintegrating dosage form where a (eating layer of an active substance (e.g. for masking a taste) is protected.

The term "orally disintegrating dosage form" which is used in the present invention means a tablet that has a hardness of 30 N (3061.22 gf) or more and disintegrates in the oral cavity within 60 seconds. Among dosage forms for oral administration, commercially available in various types of predicts, which are easy to be taken by old persons or children having a poor swallowing force and which can be easily carried the dosage forms because it is unnecessary to take the dosage form in conjunction with water, are solid-type orally disintegrating dosage forms.

Since the orally disintegrating dosage form rapidly disintegrates in the oral cavity, the taste is important in administration. In the case when the orally disintegrating dosage form that contains the active substance having the bitter taste or the unpleasant taste disintegrates by saliva in the oral cavity to enable a patient to feel the bitter taste or the unpleasant taste, the form is less tolerable. Thus, in order to manufacture the orally disintegrating dosage form with the active substance having the bitter taste or the unpleasant taste, the unpleasant taste of the active substance should be masked.

In the present invention, in order to prevent the coating layer for the active substance having the bitter taste or the unpleasant taste from being destroyed while the active substance is shaped into the tablet, the buffer having a predetermined particle size (0.1 to 10 times larger in diameter than the coated active substance) and lower hardness than the coated active substance (less than 1 time) is used at the weight ratio of 5 or less with respect to the active substance including the coating layer (preferably, the weight ratio of 0.1 to 3). Unlike the buffer, the shield having the particle size that is larger than that of the active substance including the coating layer (1 to 10 times larger than the mated active substance) and the hardness that is higher than that of the coated active substance (more than 1 time and 20 times or less) is used at the weight ratio of 3 or less with respect to the coated active substance (preferably, the weight ratio of 0.1 to 2). Sugar alcohols (sugar alcohols are not limited to sugars that is allowed during the production of drugs, and examples of the sugar alcohols may include sugar alcohols, lactoses, white sugars, glucoses, and oligosaccharides that are represented by mannitol, xylitol, sorbitol, erythritol, maltitol, and maltose) that are typically used in the orally disintegrating dosage form, and one or more super-disintegrants or one or more disintegrants are contained, and one or more types of excipients that are typically used are mixed to manufacture the orally disintegrating dosage form that has the hardness of 30 N (3061.22 gf) or more and disintegrates in the oral cavity within 60 seconds.

Since the buffer that is used in the present invention has the hardness that is lower than that of the coated active substance and is destroyed before the coating layer of the active substance is destroyed in order to buffer pressure which is applied while tableting the dosage form, the pressure which is applied to the coating layer of the active substance may be minimized. In addition, the shields, which have the higher hardness and larger particle size than the coated active substance, prevent direct pressure applied to the active substance, and at as a secondary buffering agent so that the coated active substance and the buffer which is destroyed by pressure are disposed in the spaces formed during the tableting process.

Therefore, in the present invention, one or more types of buffer that are destroyed before the coating layer of the active substance is destroyed and have lower hardness and one or more types of shield that can buffer the pressure for a predetermined time so that the coated active substance and the destroyed buffer are disposed in the spaces formed during the tableting process and have higher hardness and larger size than the active substance are mixed with each other to protect the coating layer. The particle size of each of the buffer and the shield may be varied according to the particle size of the coated active substance, and the various types of buffer and shield may be used.

If lesser amount of buffer than the above-mentioned weight ratio is used, a portion of a coating layer of an active substance may be destroyed since the amount of the buffer that is destroyed in advance according to the pressure applied during the shaping is less than the amount that is required for protection. Consequently, the active substance may be exposed which allows the patient to feel the bitter taste. The amount of the shield also plays an important role, and if the amount deviates from the above-mentioned range, pressure may be applied to the coating layer of the active substance to muse damages to the coating layer.

Examples of the excipient that may be used as buffer or shield in the present invention include isomalt, mannitol, dried mannitol, crystalline mannitol, maltitol, lactose, glucose, lactitol, trehalose, dextrate, white sugar, white sugar for direct tableting, sorbitol, xylitol, granular mannitol, aspartame, acesulfame, acesulfame potassium, saccharin sodium, a cellulose polymer (ethyl cellulose, hydroxypropyl cellulose, hydroxypropylmethyl cellulose, cellulose acetate, cellulose acetate phthalate, hydroxypropylmethylcellulose phthalate, hydroxypropylmethylcellulose succinate phthalate, cellulose acetate, cellulose acetate trimellitate, cellulose acetate butyrate, carboxymethyl cellulose, microcrystalline cellulose or the like), or other typically used excipient, but examples of the excipient are not limited thereto.

In coating of the active substance according to the present invention, a method of masking a taste and a flavor is not limited, and examples thereof may include: a coating method using a spray drier; forming a coating layer outside of an active substance using a fluidized bed water, coagulation coating; microencapsulation; micro-granulation; ionic resin absorption process; coating by a polymer after an arrive substance is applied on a seed; preparing matrix; and all other technique which can mask a taste or a flavor of an active substance.

In addition, the wave substance that is used in the present invention contains a pharmaceutical compound or chemical material that is capable of being orally administered. Examples of a drug that is useful in the present invention may include antibiotics, gastrointestinal tract (GIT) regulators, anti-viral medicines, analgesics, anesthetics, anoretics, antarthritics, antiashmatic drugs, antispasmodics, antidepressants, antidiabetic drugs, antidiarrheal agents, antihistaminic drug, anti-inflammatory agent, antiemetic drugs, antineoplastics, antiparkinsonism drugs, antipruritics, antipsychotics, antipyretics, antispasmodics, H2 antogonists, cardiovascular drugs, antiarrhythmic agents, antihypertensive agents, ACE inhibitors, diuretics, vasodilators, hormones, narcotics, immuno suppressants, muscle relaxants, parasympatholytic drugs, parasympathomimetic drugs, psychostimulants, sedatives, migraine drugs, antituberculosis drug, ataractics and the like. Any solid medicines having bitter taste or other unpleasant tastes, which should be masked, may be used in the present invention. The term "drug" includes nutritional supplements such as vitamins and minerals. One specific example of the active substance may be hydrochloride itopride.

MODE FOR THE INVENTION

In the following Examples, a detailed description will be given of a method for manufacturing an orally disintegrating dosage form while a coating layer for preventing a bitter taste or an unpleasant taste of an active substance wording to the present invention is protected, but the scope of the present invention is not limited thereto.

EXAMPLE 1

Purpose: Preparation of an orally disintegrating dosage form comprising isomalts and mosaprides coated with the mixture of the methacrylic acid-ethyl acrylate copolymer and ethyl cellulose (I)

After a seed (Cellet®) was coated with an active substance, mosapride, using Glatt fluidized bed coater, and then it was coated with a solution of 80 g of the methacrylic aid-ethyl acrylate copolymer Eudragit (Eudragit® E 100) and 20 g of ethyl cellulose in 95% ethanol by using the Glatt® fluidized bed water, wherein the weight ratio of the solution to the mosapride was 2. The coated mosapride passed through an 40 mesh sieve, and then the particles having the particle size in the range of 150 to 425 fan (hardness: 69.88 gf, see Experimental Example 3) that remained on 100 mesh sieve were selected by using the Ro-Tap® E test sieve shaker. After that, an orally disintegrating dosage form was manufactured according to the formulation that was described in the following Table 1. The buffer used was isomalt GalenIQ® 721 (hardness: 15.02 gf, and particle size: 200 to 240 μm), and the shield was isomalt GalenIQ® 981 (hardness: 679.11 gf, and particle size: 750 to 790 μm).

TABLE 1

| Composition | Addition amount (g) | Weight ratio (%) |
|---|---|---|
| Coated Mosapride (mosapride, 5 mg) | 125 | 31.25 |
| Dried mannitol | 138 | 34.5 |
| Isomalt (GalenIQ ® 721) | 30 | 7.5 |
| Isomalt (GalenIQ ® 981) | 20 | 5 |
| Crospovidone | 70 | 17.5 |
| flavored sweetener | 15 | 3.75 |
| Lubricant | 2 | 0.5 |

EXAMPLE 2

Purpose: Preparation of the orally disintegrating dosage form comprising isomalts and mosaprides coated with the mixture of methacrylic aid-ethyl acrylate copolymer and ethyl cellulose (II)

The same procedure as that in Example 1 was performed to obtain the coated mosapride. The coated mosapride passed through an 200 mesh sieve, and then the particles having the particle size in the range of 63 to 75 μm (hardness: 39.87 gf) that remained on 230 mesh sieve were selected. The buffer used was isomalt GalenIQ® 800 (hardness: 13.54 gf, and particle size: 50 μm or less), and the shield was isomalt GalenIQ® 960 (hardness: 255.48 gf, and particle size: 360 to 400 μm).

TABLE 2

| Composition | Addition amount (g) | Weight ratio (%) |
|---|---|---|
| Coated Mosapride | 125 | 31.25 |
| Dried mannitol | 138 | 34.5 |
| Isomalt (GalenIQ ® 800) | 38 | 9.5 |
| Isomalt (GalenIQ ® 960) | 12 | 3 |
| Crospovidone | 70 | 17.5 |
| flavored sweetener | 15 | 3.75 |
| Lubricant | 2 | 0.5 |

EXAMPLE 3

Purpose: Preparation of an orally disintegrating dosage form comprising isomalts and hydrochloride itopride coated with the mixture of methacrylic acid-ethyl acrylate copolymer and ethyl cellulose Hydrochloride itopride was coated with a solution of 80 g of the methacrylic aid-ethyl acrylate copolymer Eudragit (Eudragit® E 100) and 20 g of ethyl cellulose in 95% ethanol by using the Glatt® fluidized bed water, wherein the weight ratio of the solution to the hydrochloride itopride was 1.5. The coated hydrochloride itopride passed through an 40 mesh sieve, and then the particles having the particle size in the range of 150 to 425 μm (hardness: 67.83 gf, see Experimental Example 3) that remained on 100 mesh sieve were selected by using the Ro-Tap® E test sieve shaker. After that, an orally disintegrating dosage form was manufactured according to the formulation that was described in the following Table 3. The buffer used was isomalt GalenIQ® 721 (hardness: 15.02 gf, and particle size: 200 to 240 μm), and the shield was isomalt GalenIQ® 980 (hardness: 996.57 gf, and particle size: 810 to 850 μm).

TABLE 3

| Composition | Addition amount (g) | Weight ratio (%) |
|---|---|---|
| Coated Hydrochloride Itopride | 125 | 31.25 |
| Dried mannitol | 138 | 34.5 |
| Isomalt (GalenIQ ® 721) | 26 | 6.5 |
| Isomalt (GalenIQ ® 980) | 24 | 6 |
| Crospovidone | 70 | 17.5 |
| flavored sweetener | 15 | 3.75 |
| Lubricant | 2 | 0.5 |

EXAMPLE 4

Purpose: Preparation of an orally disintegrating dosage form comprising cellulose, calcium carbonate and irbesartan coated with the mixture of methacrylic aid-ethyl acrylate copolymer and ethyl cellulose (III)

After a seed (Cellet®) was coated with an active substance, irbesartan, using Glatt fluidized bed water, and then it was coated with a solution of 80 g of the methacrylic add-ethyl acrylate copolymer Eudragit (Eudragit® E 100) and 20 g of ethyl cellulose in 95% ethanol by using the Glatt fluidized bed water, wherein the weight ratio of the solution to the irbesartan was 0.5. The coated irbesartan were passed through an 30 mesh sieve, and then the particles having the particle size in the range of 425 to 600 μm (hardness: 156.11 gf) that remained on 40 mesh sieve were selected by using the Ro-Tap® E test sieve shaker. After that, an orally disintegrating dosage form was manufactured according to the formulation that was described in the following Table 4. The buffer used was cellulose (ARBOCEL® A300) (hardness: 36.08 gf, 200 μm), and the shield was calcium carbonate (VIVAPRESS® Ca800; hardness 579.37 gf, particle size 710~850 μm remained on 25 mesh sieve after passing 20 mesh sieve).

TABLE 4

| Composition | Addition amount (g) | Weight ratio (%) |
|---|---|---|
| Coated Irbesartan | 125 | 31.25 |
| Dried mannitol | 138 | 34.5 |
| Cellulose (ARBOCEL ® A300) | 40 | 10 |
| Calcium Carbonate (VIVAPRESS ® Ca800) | 10 | 2.5 |
| Crospovidone | 70 | 17.5 |
| flavored sweetener | 15 | 3.75 |
| Lubricant | 2 | 0.5 |

EXAMPLE 5

Purpose: Preparation of an orally disintegrating dosage form comprising sorbitol, seed-type sugar and domperidon coated with methacrylic acid-ethyl acrylate copolymer Domperidon was dissolved in acid ethanol (adjusted to pH 3.5 using 0.08M citrate, and then a seed (Cellet®) was coated with it using Glatt® fluidized bed coater. The coated seed, in turn, was coated with 1 weight ratio of methacrylic acid-ethyl acrylate copolymer in ethanol. The coated products were passed through an 50 mesh sieve, and then the particles having the particle size in the range of 250 to 300 μm (hardness: 103.38 gf) that remained on 60 mesh sieve were selected by using the Ro-Tap® E test sieve shaker. After that, an orally disintegrating dosage form was manufactured according to the formulation that was described in the following Table 5. The buffer used was sorbitol (hardness: 43.12 gf, and particle size: 200 to 240 μm), and the shield was sugar spheres (NON PAREIL® 101 (hardness: 857.66 gf, particle size 710~850 μm).

TABLE 5

| Composition | Addition amount (g) | Weight ratio (%) |
|---|---|---|
| Coated Domperidon | 30 | 29.13 |
| Dried mannitol | 35 | 33.98 |
| Sorbitol | 8 | 7.77 |
| Sugar Spheres (NON PAREIL ® 101) | 5 | 4.85 |
| Croscarmellose sodium | 20 | 19.42 |
| Essence of Strawberry-aroma | 2.5 | 2.43 |
| Sucralose | 2 | 1.94 |
| Lubricant | 0.5 | 0.48 |

EXAMPLE 6

Purpose: Preparation of an orally disintegrating dosage form comprising sildenafil lactate coated with polyvinylacetaldiethylamino acetate and noncrystalline cellulose granules Sildenafil lactate was coated with a solution of 95 g of polyvinylacetal diethylamino acetate and 5 g of triethyl citrate in 95% ethanol by using a fluidized bed coater, wherein the weight ratio of the solution to the sildenafil lactate was 1.5. The coated sildenafil lactate were passed through an 80 mesh sieve, and then the particles having the particle size in the range of 150 to 180 μm (hardness: 68.33 gf) that remained on 100 mesh sieve were selected by using the Ro-Tap® E test sieve shaker. After that, an orally disintegrating dosage form was manufactured according to the formulation that was described in the following Table 6. In order to get buffer (a), 4% solution of the hydroxy propyl cellulose (HPC-LF) was used as the binding solution to granulate a cellulose by using the high-speed granulator, and then the granules were dried by blowing air at 30° C. and then passed through 60 mesh sieve, and then the particles having the particle size in the range of 212 to 250 μm (hardness: 24.37 gf) that remained on 70 mesh sieve were selected by using the Ro-Tap® E test sieve shaker. In order to get shield (b), the same procedure was performed to get cellulose granules, which were then dried by blowing air at 60° C. and passed through 40 mesh sieve, and then the particles having the particle size in the range of 355 to 425 μm (hardness: 169.46 gf) that remained on 45 mesh sieve were selected.

TABLE 6

| Composition | Addition amount (g) | Weight ratio (%) |
| --- | --- | --- |
| Sildenafil lactate | 125 | 31.25 |
| Dried mannitol | 138 | 34.5 |
| Non-crystalline cellulose granule (a) | 30 | 7.5 |
| Non-crystalline cellulose granule (b) | 20 | 5 |
| Crospovidone | 70 | 17.5 |
| flavored sweetener | 15 | 3.75 |
| Lubricant | 2 | 0.5 |

EXAMPLE 7

Purpose: Preparation of an orally disintegrating dosage form comprising spray-dried lactose, lactose granule and ibupropen coated with the mixture of methacrylic acid-ethyl acrylate copolymer and ethyl cellulose Ibupropen was coated with a solution of 80 g of the methacrylic acid-ethyl acrylate copolymer Eudragit (Eudragit® E 100) and 20 g of ethyl cellulose in 95% ethanol by using the Glatt® fluidized bed coater, wherein the weight ratio of the solution to the ibupropen was 1.5. The coated ibupropen were passed through an 80 mesh sieve, and then the particles having the particle size in the range of 150 to 180 μm (hardness: 34.02 gf) that remained on a 100 mesh sieve were selected by using the Ro-Tap® E test sieve shaker. After that, an orally disintegrating dosage form was manufactured according to the formulation that was described in the following Table 7. The buffer used was Tablettose® 80 (hardness: 16.38 gf, particle size in the range of 160 to 180 μm) and the shield was a lactose granule manufactured by the following procedure: 10% solution of the hydroxy propyl cellulose (HPC-LF) was used as the binding solution to granulate lactose by using the high-speed granule device, and then the granules were dried by blowing air at 50° C. and then through a 35 mesh sieve, and then the particles having the particle size in the range of 355 to 500 μm (hardness: 162.07 gf) that remained on a 45 mesh sieve were selected by using the Ro-Tap® E test sieve shaker.

TABLE 7

| Composition | Addition amount (g) | Weight ratio (%) |
| --- | --- | --- |
| Coated Ibupropen | 500 | 31.25 |
| Dried mannitol | 552 | 34.5 |
| Tablettose ® 80 | 120 | 7.5 |
| Lactose granule | 80 | 5 |
| Bean polysaccharide | 280 | 17.5 |
| xylitol | 30 | 1.88 |
| Aspartame | 20 | 1.25 |
| Essence of Vanilla-aroma | 10 | 0.62 |
| Lubricant | 8 | 0.5 |

COMPARATIVE EXAMPLE 1

Purpose: Preparation of the orally disintegrating dosage form comprising mosaprides coated with the mixture of methacrylic acid-ethyl acrylate copolymer and ethyl cellulose and isomalts The orally disintegrating dosage form was manufactured by using the coated mosapride that was selected in Example 1 (hardness: 69.88 gf, and particle size: 150 to 425 μm) wording to the formulation shown in Table 8. The used buffer was isomalt GalenIQ® 721 (hardness: 15.02 gf, and particle size: 200 to 240 μm), and the shield was GalenIQ® 981 (hardness: 679.11 gf, and particle size: 750 to 790 μm).

TABLE 8

(unit: % by weight)

| Composition | Comparative Example 1-1 | Comparative Example 1-2 |
| --- | --- | --- |
| Coated Mosapride | 31.25 | 31.25 |
| Dried mannitol | 34.5 | 34.5 |
| GalenIQ ® 721 | 12.5 | 0 |
| GalenIQ ® 981 | 0 | 12.5 |
| Crospovidone | 17.5 | 17.5 |
| flavored sweetener | 3.75 | 3.75 |
| Lubricant | 0.5 | 0.5 |

COMPARATIVE EXAMPLE 2

Purpose: Preparation of the orally disintegrating dosage form comprising mosaprides coated with the mixture of methacrylic aid-ethyl acrylate copolymer and isomalts The orally disintegrating dosage form was manufactured by using the coated mosapride that was selected in Example 2 (hardness: 39.87 gf, and particle size: 63 to 75 μm) according to the formulation shown in Table 9. The used buffer was isomalt GalenIQ® 800 (hardness: 13.54 gf, and particle size: 50 μm or less), and the shield was GalenIQ® 721 (hardness: 15.02 gf, and particle size: 200 to 240 μm).

TABLE 9

| Composition | Addition amount (g) | Weight ratio (%) |
| --- | --- | --- |
| Coated Mosapride | 125 | 31.25 |
| Dried mannitol | 138 | 34.5 |
| Isomalt (GalenIQ ® 800) | 38 | 9.5 |
| Isomalt (GalenIQ ® 721) | 12 | 3 |

TABLE 9-continued

| Composition | Addition amount (g) | Weight ratio (%) |
|---|---|---|
| Crospovidone | 70 | 17.5 |
| flavored sweetener | 15 | 3.75 |
| Lubricant | 2 | 0.5 |

COMPARATIVE EXAMPLE 3

Purpose: Preparation of the orally disintegrating dosage form comprising isomalt and irbesartan coated with the mixture of methacrylic acid-ethyl acrylate copolymer and ethyl cellulose The orally disintegrating dosage form was manufactured by using the coated irbesartan that was selected in Example 4 (hardness: 156.11 gf, and particle size: 425 to 600 μm) according to the formulation shown in Table 10. The used buffer was isomalt GalenIQ® 960 (hardness: 255.48 gf, and particle size: 360~400 μm), and the shield was GalenIQ® 980 (hardness: 996.57 gf, and particle size: 810 to 850 μm).

TABLE 10

| Composition | Addition amount (g) | Weight ratio (%) |
|---|---|---|
| Coated Irbesartan | 125 | 31.25 |
| Dried mannitol | 138 | 34.5 |
| Isomalt (GalenIQ ® 960) | 38 | 9.5 |
| Isomalt (GalenIQ ® 980) | 12 | 3 |
| Crospovidone | 70 | 17.5 |
| flavored sweetener | 15 | 3.75 |
| Lubricant | 2 | 0.5 |

COMPARATIVE EXAMPLE 4

Purpose: Preparation of an orally disintegrating dosage form comprising sildenafil lactate coated with polyvinylacetaldiethylamino acetate and non-crystalline cellulose granules The orally disintegrating dosage form was manufactured by using the coated sildenafil lactate that was selected in Example 6 (hardness: 68.33 gf, and particle size: 150 to 180 μm) according to the formulation shown in Table 11. In order to get buffer (a), 7% solution of the hydroxy propyl cellulose (HPC-LF) was used as the binding solution to granulate a cellulose by using the high-speed granulator, and then the granules were dried by blowing air at 40° C. and then passed through a 70 mesh sieve, and then the particles having the particle size in the range of 180 to 212 μm (hardness: 70.01 gf) that remained on an 80 mesh sieve were selected by using the Ro-Tap® E test sieve shaker. In order to get shield (b), the same granules were through a 25 mesh sieve, and then the particles having the particle size in the range of 600 to 710 μm (hardness: 70.01 gf) that remained on 30 mesh sieve were selected.

TABLE 11

| Composition | Addition amount (g) | Weight ratio (%) |
|---|---|---|
| Sildenafil lactate | 125 | 31.25 |
| Dried mannitol | 138 | 34.5 |
| Non-crystalline cellulose granule (a) | 30 | 7.5 |
| Non-crystalline cellulose granule (b) | 20 | 5 |
| Crospovidone | 70 | 17.5 |
| flavored sweetener | 15 | 3.75 |
| Lubricant | 2 | 0.5 |

COMPARATIVE EXAMPLE 5

Purpose: Preparation of an orally disintegrating dosage form comprising sildenafil lactate coated with polyvinylacetaldiethylamino acetate and non-crystalline cellulose granules The coated sildenafil lactates in Example 6 were passed through a 50 mesh sieve, and then the particles having the particle size in the range of 250 to 300 μm (hardness: 89.12 gf) that remained on a 60 mesh sieve were selected by using the Ro-Tap® E test sieve shaker. After that, the orally disintegrating dosage form was manufactured according to the formulation shown in Table 12. In order to get buffer (a), 3% solution of the hydroxy propyl cellulose (HPC-LF) was used as the binding solution to granulate a non-crystalline cellulose by using the high-speed granulator, and then the granules were dried by blowing air at 30° C. and then passed through a 70 mesh sieve, and then the particles having the particle size in the range of 180 to 212 μm (hardness: 21.47 gf) that remained on an 80 mesh sieve were selected by using the Ro-Tap® E test sieve shaker. In order to get shield (b), 10% solution of the hydroxy propyl cellulose (HPC-LF) was used as the binding solution in granulating in the same procedure, and then the granules were dried by blowing air at 60° C. and obtained the particles having the same size as buffer (a) (hardness: 173.12 gf).

TABLE 12

| Composition | Addition amount (g) | Weight ratio (%) |
|---|---|---|
| Sildenafil lactate | 125 | 31.25 |
| Dried mannitol | 138 | 34.5 |
| Non-crystalline cellulose granule (a) | 30 | 7.5 |
| Non-crystalline cellulose granule (b) | 20 | 5 |
| Crospovidone | 70 | 17.5 |
| flavored sweetener | 15 | 3.75 |
| Lubricant | 2 | 0.5 |

COMPARATIVE EXAMPLE 6

Purpose: Preparation of an orally disintegrating dosage form comprising cellulose, calcium carbonate and irbesartan coated with the mixture of methacrylic acid-ethyl acrylate copolymer and ethyl cellulose The orally disintegrating dosage form was manufactured by using the coated irbesartan that was selected in Example 4 (hardness: 156.11 gf, and particle size: 425 to 600 μm) according to the formulation shown in Table 13. The buffer used was cellulose (ARBOCEL® A300) (hardness: 36.08 gf, 200 μm), and the shield was calcium carbonate (VIVAPRESS® Ca800; hardness 579.37 gf, particle size 710~850 μm remained on 25 mesh sieve after passing 20 mesh sieve).

TABLE 13

| Composition | Addition amount (g) | Weight ratio (%) |
|---|---|---|
| Coated Irbesartan | 125 | 31.25 |
| Dried mannitol | 138 | 34.5 |

TABLE 13-continued

| Composition | Addition amount (g) | Weight ratio (%) |
|---|---|---|
| Cellulose (ARBOCEL ® A300) | 10 | 2.5 |
| Calcium Carbonate (VIVAPRESS ® Ca800) | 40 | 10 |
| Crospovidone | 70 | 17.5 |
| flavored sweetener | 15 | 3.75 |
| Lubricant | 2 | 0.5 |

EXPERIMENTAL EXAMPLE 1

Purpose: Test of the hardness of the particle

The hardness of the buffer, the shield, and the particles of the active substance including the coating layer that were used in the Examples were measured by using a physical property analyzer (Texture Analyser, TA.AX® plus, Stable micro systems, UK), and the results are described in Table 14.

TABLE 14

(unit: gf)

| | Coated Active Substance | Buffer | Shield |
|---|---|---|---|
| Example 1 | 69.88 | 15.02 | 679.10 |
| Example 2 | 39.87 | 13.54 | 255.48 |
| Example 3 | 67.83 | 15.02 | 996.57 |
| Example 4 | 156.11 | 36.08 | 579.37 |
| Example 5 | 103.38 | 43.12 | 857.66 |
| Example 6 | 68.33 | 24.37 | 169.46 |
| Example 7 | 34.02 | 16.38 | 162.07 |
| Comp. Example 1-1 | 69.88 | 15.02 | — |
| Comp. Example 1-2 | 69.88 | — | 679.11 |
| Comp. Example 2 | 39.87 | 13.54 | 15.02 |
| Comp. Example 3 | 156.11 | 255.48 | 996.57 |
| Comp. Example 4 | 68.33 | 70.01 | 70.01 |
| Comp. Example 5 | 89.12 | 21.47 | 173.12 |
| Comp, Example 6 | 156.11 | 36.08 | 579.37 |

EXPERIMENTAL EXAMPLE 2

Purpose: Test of the solubility in artificial saliva

After 12 mM of potassium dihydrogen phosphate solution, 40 nM of sodium chloride solution, and 1.5 nM of calcium chloride solution were mixed with each other, the pH was adjusted to 6.2 with sodium hydroxide to prepare artificial saliva. Each of the samples of Examples 1 to 7 and Comparative Examples 1 to 6 was disintegrated in 100 ml of the artificial saliva, was left for 10 min, and then assayed to determine the content of the released active substance. The results are described in Table 15. The higher content shows the more of the mating layers are destroyed and the release of active substance within the oral cavity.

TABLE 15

(unit: %)

| | Average content (%) |
|---|---|
| Example 1 | 1.39 |
| Example 2 | 2.26 |
| Example 3 | 2.89 |
| Example 4 | 1.75 |
| Example 5 | 3.64 |
| Example 6 | 3.18 |

TABLE 15-continued (unit: %)

| | Average content (%) |
|---|---|
| Example 7 | 2.44 |
| Comp. Example 1-1 | 59.48 |
| Comp. Example 1-2 | 65.15 |
| Comp. Example 2 | 87.64 |
| Comp. Example 3 | 70.11 |
| Comp. Example 4 | 79.88 |
| Comp. Example 5 | 45.34 |
| Comp. Example 6 | 87.44 |

In the case of the compositions prepared in Examples 1 to 7, which include the buffer having lower hardness than the coated active substance and the shield having higher hardness and larger particle size than the coated active substance, with the weight ratio of the buffer to the shield of 1 or more, the degree of destroying of the coating layer in the artificial saliva was low. However, in the use when buffer or shield was used alone (Comparative Example 1), when the hardness of shield was lower than that of the particle of the coated active substance (Comparative Example 2), when the hardness of the first protective excipient was higher than that of the particle of the coated active substance (Comparative Example 3), when the buffer and the shield had the same hardness to each other (Comparative Example 4), when the particle of the shield was smaller than that of the particle of the coated active substance (Comparative Example 5), and when the weight ratio of the buffer to the shield was less than 1 (Comparative Example 6), the degree of destroying of the coating layer was high.

EXPERIMENTAL EXAMPLE 3

Purpose: Sensory evaluation

The orally disintegrating dosage forms that were manufactured in Examples 1 to 4 and 7 and Comparative Examples 1 to 3 and 6 were administered to 15 women and 15 men of 20- to 50-aged healthy adult, and the degree of bitter taste each person felt was checked 2 minutes after it was taken. The results are described in Table 16. One dosage form was administered every 6 hours, and the test was performed for 5 days.

(Degree of Bitter Taste)

The patient does not feel bitter taste at all: 0
The patient feels bitter taste just a little: 1
The patient feels bitter taste just a little more: 2
The patient feels bitter taste: 3
The patient feels bitter taste but can bear the bitter taste: 4
The patient feels bitter taste and cannot bear the bitter taste: 5

TABLE 16

| | Degree of bitter taste (the number of persons) | | | | | |
|---|---|---|---|---|---|---|
| | 0 | 1 | 2 | 3 | 4 | 5 |
| Example 1 | 26 | 4 | 0 | 0 | 0 | 0 |
| Example 2 | 16 | 13 | 1 | 0 | 0 | 0 |
| Example 3 | 16 | 14 | 0 | 0 | 0 | 0 |
| Example 4 | 18 | 19 | 3 | 0 | 0 | 0 |
| Example 7 | 16 | 14 | 0 | 0 | 0 | 0 |
| Comp. Example 1-1 | 0 | 0 | 5 | 13 | 11 | 1 |
| Comp. Example 1-2 | 0 | 0 | 4 | 10 | 15 | 1 |
| Comp. Example 2 | 0 | 0 | 0 | 8 | 18 | 4 |

TABLE 16-continued

| | Degree of bitter taste (the number of persons) | | | | | |
|---|---|---|---|---|---|---|
| | 0 | 1 | 2 | 3 | 4 | 5 |
| Comp. Example 3 | 0 | 0 | 0 | 7 | 12 | 11 |
| Comp. Example 6 | 0 | 0 | 0 | 6 | 15 | 9 |

In the case of the compositions prepared in Examples 1 to 4 and 7, which include the buffer having lower hardness than the coated active substance and the shield having higher hardness and larger particle size than the coated active substance, with the weight ratio of the buffer to the shield of 1 or more, most subjects did not feel bitter taste or felt the bitter taste just a little. However, in the case when buffer or shield was used alone (Comparative Example 1), when the hardness of shield was lower than that of the particle of the coated active substance (Comparative Example 2), when the hardness of the first protective excipient was higher than that of the particle of the coated motive substance (Comparative Example 3), when the buffer and the shield had the same hardness to each other (Comparative Example 4), when the particle of the shield was smaller than that of the particle of the coated active substance (Comparative Example 5), and when the weight ratio of the buffer to the shield was less than 1 (Comparative Example 6), most subjects felt the bitter taste.

The invention claimed is:

1. A method of manufacturing an orally disintegrating tablet comprising:
    mixing
        particles of a coated active substance having a diameter in the range of about 0.1 to 1000 microns and a hardness in the range of about 34.02 to 156.11 gf,
        particles of a buffer having lower hardness than the particles of the coated active substance, said buffer particles having a hardness in the range of from 13.54 to 43.12 gf, and
        particles of a shield having higher hardness and a larger particle size than the particles of the coated active substance, said shield particles having a hardness of from 162 to 996.57 gf;
    tableting
        the mixture comprising the coated active substance particles, the buffer particles, and the shield particles at a pressure which is sufficient to fracture the buffer particles but not the active substance particles; and
    wherein prior to tableting the hardness of the buffer particles is 0.1 to less than 1 times as high as the hardness of the coated active substance particles, and
    wherein the coated active substance is selected from the group consisting of mosapride, hydrochloride itopride, irbesartan, sildenafil, domperidone, and ibupropen,
    wherein the particles of the buffer are selected from one or more of the group consisting of isomalt, cellulose, sorbitol, hydroxypropyl cellulose, and lactose, and
    wherein the particles of the shield are selected from one or more of the group consisting of isomalt, calcium carbonate, sugar spheres, cellulose, and lactose.

2. The method of claim 1, wherein prior to tableting the hardness of the shield particles is greater than 1 and less than or equal to 20 times as high as the hardness of the coated active substance particles.

3. The method of claim 2, wherein prior to tableting the hardness of the buffer particles is 0.1 to 0.7 times as high as the hardness of the coated active substance particles, and the hardness of the shield particles is 4 to 15 times as high as the hardness of the coated active substance particles.

4. The method of claim 1, wherein prior to tableting the coated active substance particles have a particle diameter in the range of 0.1 to 1000 μm, the buffer particles have a particle diameter 0.1 to 10 times as large as the particle diameter of the coated active substance particles, and the shield particles have a particle size greater than 1 and less than or equal to 10 times as large as the particle diameter of the coated active substance particles.

5. The method of claim 1, wherein prior to tableting the coated active substance particles have a particle diameter in the range of 150 to 425 μm, the buffer particles have a particle diameter 1 to 3 times as large as the particle diameter of the coated active substance particles, and the shield particles have a particle diameter greater than 1 and less than or equal to 4 times as large as the particle diameter of the coated active substance particles.

6. The method of claim 1, wherein prior to tableting the weight ratio of the buffer with respect to the coated active substance is 5 or less, and the weight ratio of the shield with respect to the coated active substance is 3 or less.

7. The method of claim 6 wherein prior to tableting the weight of the coated active substance is in the range of 1 to 1000 mg, the weight ratio of the buffer with respect to the coated active substance is in the range of 0.1 to 3, and the weight ratio of the shield with respect to the coated active substance is in the range of 0.1 to 2.

8. The method of claim 1, wherein the weight ration of the buffer with respect to the shield is at least 1.

9. The method of claim 1, further wherein the particles of buffer or the particles of the shield comprise a granulated material.

10. The method of claim 1, further comprising manufacturing a coating layer on the active substance by a process selected from the group consisting of coating using a fluidized bed coater, coating using a spray drier, coagulation coating, microencapsulation, micro-granulation, ionic resin absorption, and coating by a polymer after an active substance is applied on a seed.

11. The method of claim 1, wherein the orally disintegrating tablet disintegrates in an oral cavity within 60 seconds.

12. The method of claim 1, wherein the hardness of the orally disintegrating tablet is at least 30 N.

13. The method of claim 1, wherein the active substance is hydrochloride itopride.

14. The method of claim 1, wherein the orally disintegrating tablet comprises about 12.5 wt % of a combination of the buffer and shield.

15. The method of claim 1, wherein during said tableting the fractured buffer material is disposed in spaces formed during the tableting.

16. The method of claim 1, wherein mixing further comprises mixing about 34.5 wt % dried mannitol in addition to any mannitol present in the particles of the buffer and the particles of the shield.

17. The method of claim 11, wherein the orally disintegrating tablet disintegrates into particles having a diameter of 2 mm or less within the 60 seconds.

18. The method of claim 1, wherein the orally disintegrating tablet comprises about 29.13-31.25 wt % of the coated active substance, about 6.5-10 wt % of the buffer, and about 2.5-6 wt % of the shield.

* * * * *